United States Patent
Lei et al.

(10) Patent No.: US 11,839,412 B2
(45) Date of Patent: Dec. 12, 2023

(54) MULTI-PLANE CORTICAL BONE SCREW, BONE POSITIONING DEVICE AND POSITIONING AND USE METHOD

(71) Applicant: THE THIRD HOSPITAL OF CHANGSHA, Changsha (CN)

(72) Inventors: Qing Lei, Changsha (CN); Lei Fan, Changsha (CN); Minghui Jiang, Changsha (CN); Lihong Cai, Changsha (CN)

(73) Assignee: THE THIRD HOSPITAL OF CHANGSHA, Changsha (CN)

( * ) Notice: Subject to any disclaimer, the term of this patent is extended or adjusted under 35 U.S.C. 154(b) by 0 days.

(21) Appl. No.: 18/183,151

(22) Filed: Mar. 13, 2023

(65) Prior Publication Data
US 2023/0293209 A1 Sep. 21, 2023

(30) Foreign Application Priority Data
Mar. 17, 2022 (CN) .......................... 202210262078.5

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC .......................... A61B 17/7037; A61B 17/7032
USPC ....... 606/266, 267, 268, 269, 270, 272, 275, 606/278, 305, 308, 317, 328
See application file for complete search history.

(56) References Cited

U.S. PATENT DOCUMENTS

| | | | | |
|---|---|---|---|---|
| 9,763,700 | B1* | 9/2017 | Gregory | A61B 17/8695 |
| 2012/0221055 | A1* | 8/2012 | Copf | A61B 17/7041 606/279 |
| 2012/0232598 | A1* | 9/2012 | Hestad | A61B 17/7037 29/446 |
| 2013/0096618 | A1 | 4/2013 | Chandanson et al. | |
| 2013/0131729 | A1* | 5/2013 | Stauber | A61B 17/7035 606/267 |
| 2014/0025120 | A1* | 1/2014 | Farris | A61B 17/7035 606/300 |

(Continued)

FOREIGN PATENT DOCUMENTS

| | | |
|---|---|---|
| CN | 102596068 A | 7/2012 |
| CN | 103124534 A | 5/2013 |

(Continued)

*Primary Examiner* — Eduardo C Robert
*Assistant Examiner* — David C Comstock

(57) ABSTRACT

A multi-plane cortical bone screw includes a screw tail and a ball screw. A ball head portion is arranged at one end of the ball screw, and a thread portion is arranged at the other end thereof. The ball head portion and the screw tail are in universal connection, so that the ball screw can rotate along a conical surface relative to the screw tail. A lower end face of the screw tail close to the ball head portion is relatively rotatably connected with a side face of the screw tail. The present disclosure further discloses a bone positioning device, which includes a plurality of connection rods and a plurality of the multi-plane cortical bone screws. The screw tails are arranged in a spatial three-dimensional radial manner along side edges of a multi-edge platform, and the connection rods used for positioning a bone are connected between the screw tails.

18 Claims, 12 Drawing Sheets

(56) References Cited

U.S. PATENT DOCUMENTS

| | | | | |
|---|---|---|---|---|
| 2014/0094849 A1* | 4/2014 | Spratt | ............... | A61B 17/7032 |
| | | | | 606/257 |
| 2014/0214097 A1 | 7/2014 | Jackson et al. | | |
| 2019/0274737 A1* | 9/2019 | Biedermann | ...... | A61B 17/7032 |
| 2020/0289165 A1* | 9/2020 | Ma | ..................... | A61B 17/7005 |
| 2021/0282819 A1* | 9/2021 | Biedermann | ...... | A61B 17/7037 |

FOREIGN PATENT DOCUMENTS

| | | | |
|---|---|---|---|
| CN | 106806010 | A | 6/2017 |
| CN | 108697442 | A | 10/2018 |
| CN | 111902098 | A | 11/2020 |
| CN | 112353474 | A | 2/2021 |
| CN | 112932640 | A | 6/2021 |
| CN | 113171166 | A | 7/2021 |
| CN | 113303897 | A | 8/2021 |
| CN | 213963599 | U | 8/2021 |

* cited by examiner

MULTI-PLANE CORTICAL BONE SCREW, BONE POSITIONING DEVICE AND POSITIONING AND USE METHOD

CROSS-REFERENCE TO RELATED APPLICATION

This patent application claims the benefit and priority of Chinese Patent Application No. 202210262078.5 filed on Mar. 17, 2022, the disclosure of which is incorporated by reference herein in its entirety as part of the present application.

TECHNICAL FIELD

The present disclosure belongs to the technical field of medical apparatuses, and particularly relates to a multi-plane cortical bone screw, a bone positioning device and a positioning and use method.

BACKGROUND

Thoracolumbar decompression and internal fixation fusion is an effective therapy for thoracolumbar degenerative diseases. At present, spinal surgery is developed towards the direction of minimally invasive small incisions. Having a smaller incision length, a smaller stripping range and a shorter recovery cycle has become a common goal that spinal surgeons and patients pursue. A cortical bone trajectory screw has gradually become a preferred fixation way for the thoracolumbar degenerative diseases followed by osteoporosis due to its advantages of enhanced screw removal ability, small incision and small stripping range. In the cortical bone trajectory internal fixation technology, the cortical bone trajectory screw can penetrate through four cortical bones, i.e. the cortical bone of the isthmus of the spinal posterior column, the cortical bone on the inner side of the vertebral pedicle, the cortical bone on the outer side of the vertebral pedicle, and the cortical bone of the upper vertebral body outside the spinal middle column, so that higher resistance to pullout can be achieved. The cortical bone trajectory screw is applicable to the spinal internal fixation for patients suffering from osteoporosis. In a traditional cortical bone screw, although there is a universal rotation feature between a screw tail 1 and a ball screw 3, a connection rod 4 is directly clipped into U-shaped notches 11 of the adjacent screw tails 1, which makes it very easy to combine the cortical bone screw with the connection rod 4.

However, the flexibility of the traditional cortical bone screw is still limited. After the cortical bone screw is implanted, an orientation of a rotation angle of the U-shaped notch 11 cannot be adjusted for the second time. If the external structural shape of the cortical bone screw is changed, this cortical bone screw will block the operation or does not adapt to the shape of a human bone. Therefore, the structure of the cortical bone screw needs to be further improved. How to increase the flexibility of the cortical bone screw without destroying the external shape of the cortical bone screw is the main task.

SUMMARY

In order to solve the problems in the above prior art, the present disclosure provides a multi-plane cortical bone screw, a bone positioning device and a positioning and use method. The multi-plane cortical bone screw of the present disclosure can be pre-implanted in a cortical bone trajectory channel without blocking a surgical decompression area. A ball screw cooperates with a screw tail to rotatably adjust the position and angle of the screw, thus realizing a multi-plane adjustment function. The multi-plane cortical bone screw features with simple structure, convenience of operation, high applicability and the like.

In order to achieve the above objective, specific technical solutions of a multi-plane cortical bone screw, a bone positioning device and a positioning and use method of the present disclosure are as follows.

A multi-plane cortical bone screw includes a screw tail, a ball screw connected with the screw tail, and a chucking appliance arranged on the screw tail; a ball head portion is arranged at one end of the ball screw, and a thread portion is arranged at the other end of the ball screw; the ball head portion and the screw tail are in universal connection, and the chucking appliance limits the ball screw and the screw tail to prevent disconnection, so that the ball screw can rotate along a conical surface relative to the screw tail, and a function of multi-plane multi-angle adjustment for the ball screw relative to an axial line of the screw tail is realized; a lower end face of the screw tail close to the ball head portion is relatively rotatably connected with a side face of the screw tail.

Further, an inclined bottom plate capable of circumferentially rotating is arranged at a bottom of the screw tail; a lower end face of the inclined bottom plate is oblique; a side wall of the inclined bottom plate is long, and another side wall of the inclined bottom plate is short, so that the ball screw rotates, swings and tilts towards a short side wall of the screw tail by a larger angle c.

Further, the inclined bottom plate includes an inclined bottom plate lower component, an inclined bottom plate middle connector connected with an upper end of the inclined bottom plate lower component, and an inclined bottom plate upper component connected with an upper end of the inclined bottom plate middle connector; and the inclined bottom plate upper component is rotatably clipped into a bayonet formed in an inner side wall of the screw tail.

Further, the inclined bottom plate upper component is an annular convex ring; and the bayonet is an annular inner notch clamped with the annular convex ring in a matched manner.

Further, an axially penetrating through hole is formed in the screw tail; an opening in an end of the through hole is large, and an opening in another end is small; the ball screw passes through the end of the through hole with the large opening, and the ball head portion is movably clamped at the other end of the through hole with the small opening; and the chucking appliance is restrained in the through hole, so as to limit the degree of freedom of movement of the ball head portion along an axial direction of the screw tail.

Further, an inner slot is formed in one end of the chucking appliance; and the inner slot is of an indented structure with a curved spherical surface, which is similar to the ball head portion so that the inner slot is buckled with the ball head portion of the ball screw in a matched manner.

Further, the through hole along an inserting direction of the ball screw includes a straight hole section and a fixed section which are connected with each other in a penetrating manner, and the chucking appliance is located between the straight hole section and the fixed section.

Further, an internal thread is formed on a side wall of the straight hole section; and mutually symmetric U-shaped notches are formed in a side wall of the screw tail.

Further, the through hole of the ball screw includes a fixed section; the fixed section includes an upper first curved section and a lower second curved section which are communicated with each other, and a curvature of the second curved section is less than that of the first curved section; the first curved section is located on one side close to the chucking appliance; and a side wall clamping section of the chucking appliance is clamped with the first curved section in a matched manner.

Further, the through hole of the ball screw includes a straight hole section; a round hole groove is formed in a side wall of the screw tail that is provided with the straight hole section; an external die thimble component is inserted into the round hole groove to press the chucking appliance, so that the chucking appliance deforms to be separated from the screw tail and then is restored to the original shape.

Further, a gap is formed in a top of the lower end face of the screw tail close to the ball head portion, so that when the ball screw rotates towards a short side wall of the screw tail, the ball screw is clamped to the gap, thus increasing an inclination angle of the ball screw relative to the screw tail.

Further, the lower end face of the screw tail and a horizontal plane form an included angle a of 10°-30°, preferably 20°.

A bone positioning device includes a plurality of connection rods and further includes a plurality of the above multi-plane cortical bone screws. The screw tails are arranged in a spatial three-dimensional radial manner along side edges of a multi-edge platform, and the connection rods used for positioning a bone are connected between the screw tails of each group, wherein each group includes two screw tails.

A use and positioning method for a multi-plane cortical bone screw includes the following steps:

a step of positioning the upper vertebral body: a screw inserting point is located at 5 o'clock (on the left side of a posteroanterior view) or 7 o'clock (on the right side of the posteroanterior view) below the vertebral pedicle isthmus; a screw placement trajectory retracts 5-15° (most preferably 10°); under a tail inclination of 25° to 30°, the screw is placed along the lower boundary of the vertebral pedicle;

a step of positioning the lower vertebral body: the screw inserting point is located at 1 o'clock (on the left side of the posteroanterior view) or 11 o'clock (on the right side of the posteroanterior view) above the inferior articular process; the screw placement trajectory retracts 5-15° (most preferably 10°); under a head inclination of 25° to 30°, the screw is placed along the upper boundary of the vertebral pedicle; the screw is inserted from the needle inserting point from 1 o'clock to 7 o'clock (on the left side of the posteroanterior view), and the screw is inserted from the right side of a posteroanterior view according to a mirror image.

Further, a bottom of an upper screw canal used for mounting the multi-plane cortical bone screw points to the posterior 1/3 position of an upper end plate, and a bottom of a lower screw canal points to the posterior 1/3 position of a lower end plate, so that the multi-plane cortical bone screw in the vertebral plate and the vertebral body is the longest and ends at a central position of the end plate of the vertebral body.

The present disclosure has the following beneficial effects.

The mountable cortical bone trajectory screw provided by the present disclosure has a simple structure and can be inserted and removed, and the mounting step is convenient. There is no interference from the screw tail during decompression, which facilitates decompression and expands the decompression range, and improves the decompression range of a cortical bone trajectory technology. The lower end face of the screw tail can be relatively rotatably connected with the side surface of the screw tail. When multiple tail cap cortical bone screws are needed, the direction of the screw tail can be changed more conveniently, so that the extension space of the cortical bone screw is broadened; and the multiple multi-plane cortical bone screws can be easily connected in series, with high adaptability. In use, a needle inserting point and a needle inserting angle of the lower vertebral body are changed, so that the orientation of the screw tail of the cortical bone screw can be adjusted for the second time in a posterior surgical passage to improve the accuracy of the implanting of the cortical bone screw. If an exposure range is reduced under the condition of keeping the supporting strength unchanged, the operation can be more minimally invasive, bleeding in the operation is reduced, the operation time is shortened, and postoperative rehabilitation is accelerated.

Figure 1:
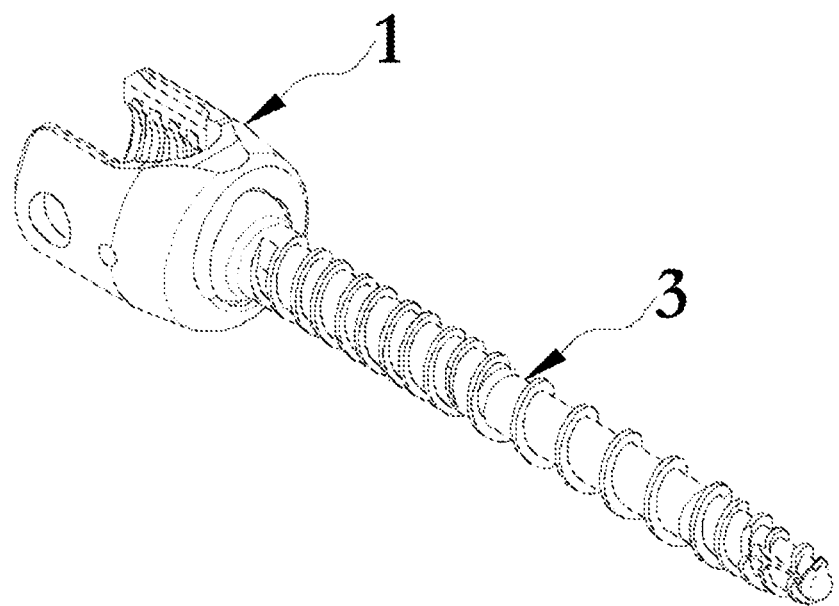
FIG. 1 is a three-dimensional diagram after a screw is assembled.
Figure 2:
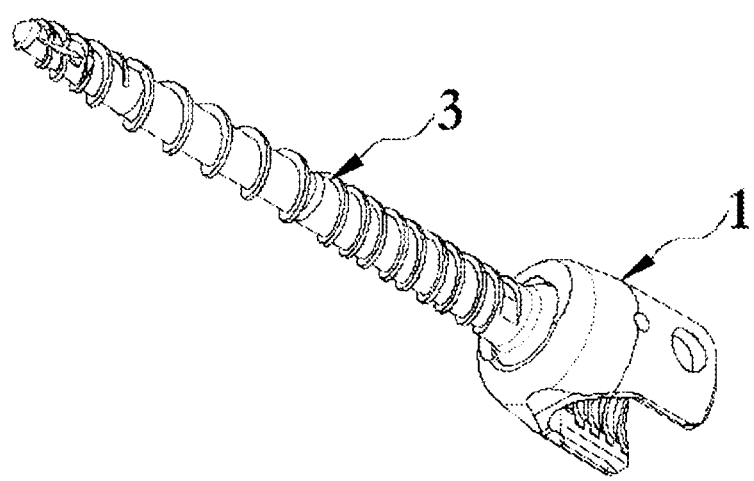
FIG. 2 is a three-dimensional diagram from another view after the screw is assembled.
Figure 3:
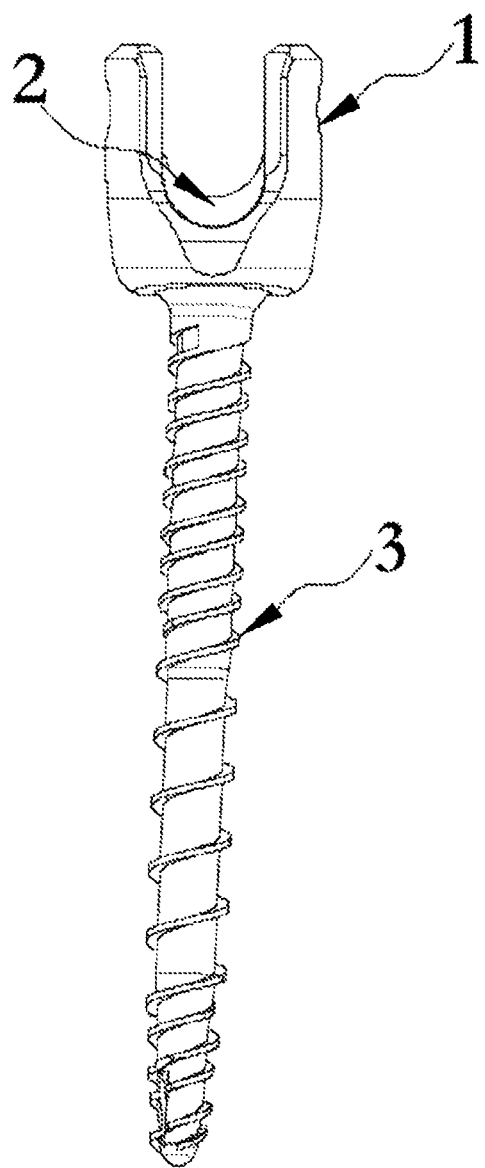
FIG. 3 is a front view after the screw is assembled.
Figure 4:
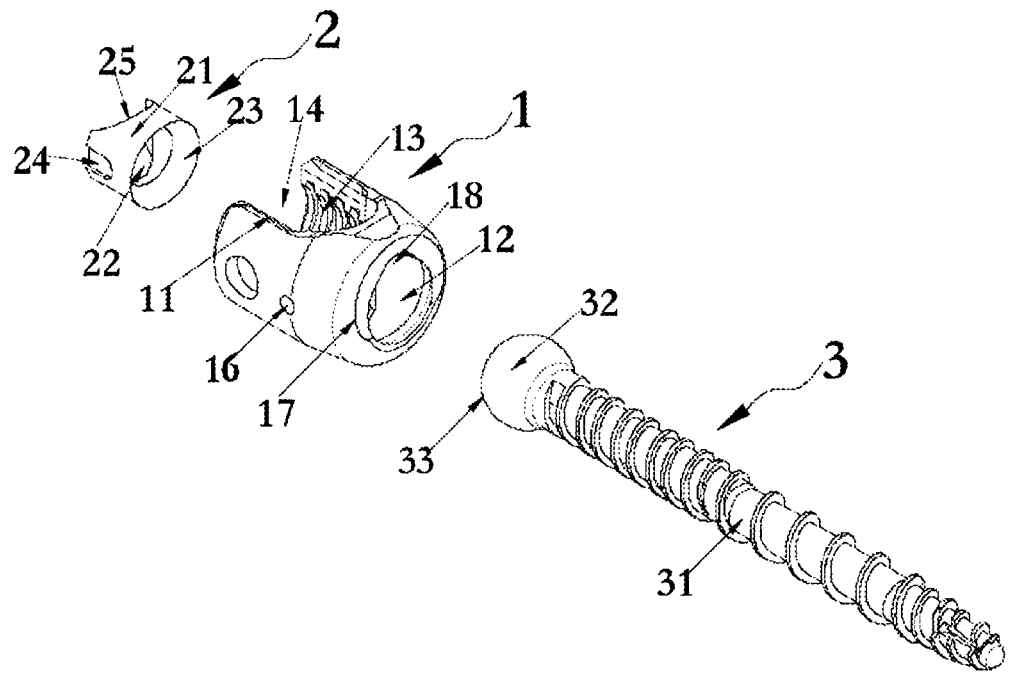
FIG. 4 is an exploded diagram of FIG. 1.
Figure 5:
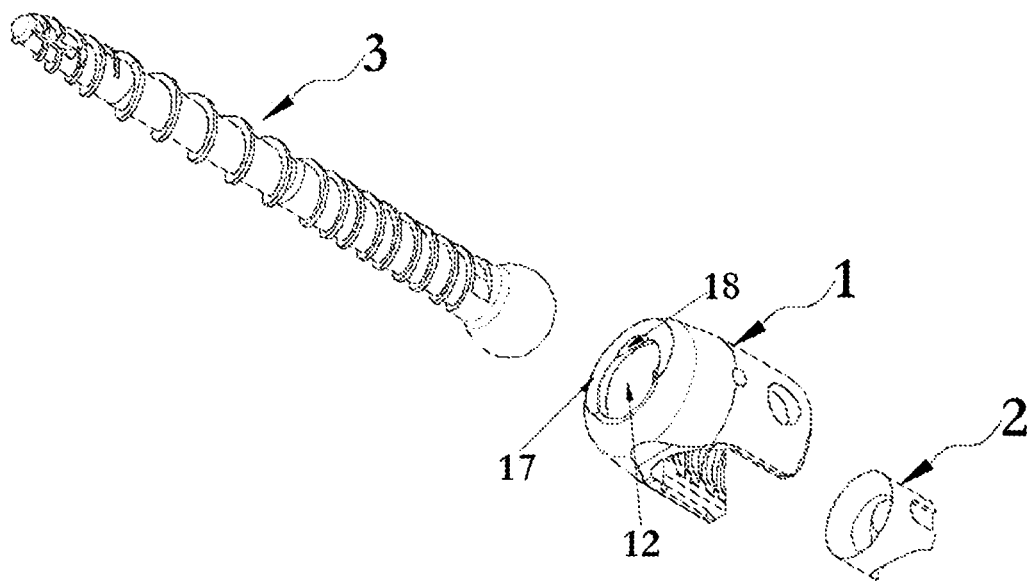
FIG. 5 is an exploded diagram of FIG. 2.
Figure 6:
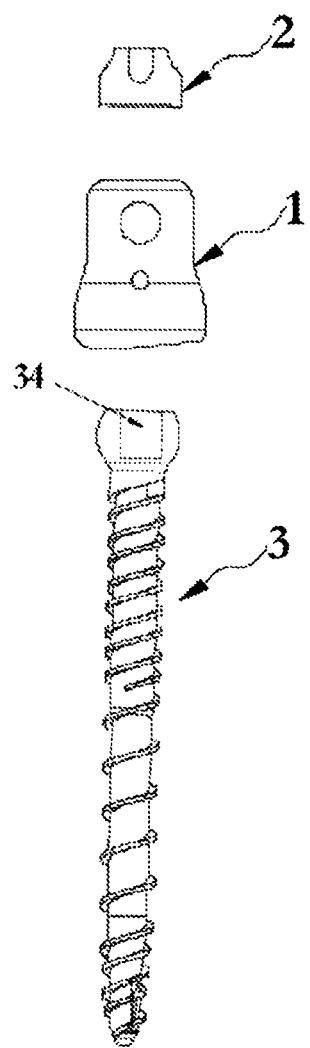
FIG. 6 is an exploded diagram of FIG. 3.
Figure 7:
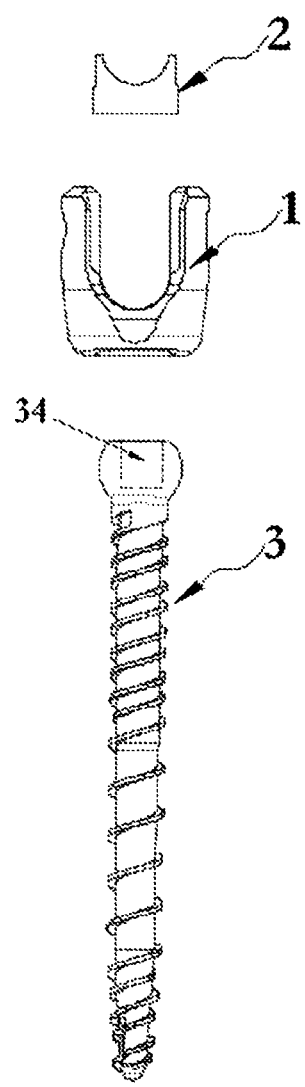
FIG. 7 is a side view of FIG. 6.

Reference Numerals: 1: screw tail; 2: chucking appliance; 3: ball screw; 4: connection rod; 5: upper end plate; 6: lower end plate; 7: vertebral pedicle isthmus; 8: upper vertebral body; 9: lower vertebral body; 11: U-shaped notch; 12: through hole; 13: internal thread; 14: straight hole section; 16: round hole groove; 17: inclined bottom plate; 171: inclined bottom plate lower component; 172: inclined bottom plate upper component; 173: inclined bottom plate middle connector; 18: gap; 19: bayonet; 21: side wall; 22: central hole; 23: inner slot; 24: clamping section; 25: U-shaped gap; 31: thread portion; 32: ball head portion; 33: plane; and 34: ball head positioning slot.

DETAILED DESCRIPTION OF THE EMBODIMENTS

The terminology used herein for the purpose of describing particular examples is not intended to be limiting for further examples. Whenever a singular form such as "a" "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises", "comprising", "includes" and/or "including", when used, specify the presence of the stated features, integers, steps, operations, processes, acts, elements and/or components, but do not preclude the presence or addition of one or more other features, integers, steps, operations, processes, acts, elements, components and/or any group thereof.

In order to better understand the objectives, structures and functions of the present disclosure, a multi-plane cortical bone screw, a bone positioning device and a positioning and use method of the present disclosure will be further described in detail below in combination with FIG. 1 to FIG. 16.

The present disclosure discloses a multi-plane cortical bone screw, including a screw tail 1 and a ball screw 3 connected with the screw tail 1. A ball head portion 32 is arranged at one end of the ball screw 3, and a thread portion 31 is arranged at the other end of the ball screw 3. The ball head portion 32 and the screw tail 1 are in universal connection, and a chucking appliance 2 limits the ball screw 3 and the screw tail 1 to prevent disconnection, so that the ball screw 3 can rotate along a conical surface relative to the screw tail 1, and a function of multi-plane multi-angle adjustment for the ball screw 3 relative to an axial line of the screw tail 1 is realized. A lower end face of the screw tail 1 close to the ball head portion 32 is relatively rotatably connected with a side face of the screw tail 1. The cortical bone screw of the present disclosure has a simple structure and can be inserted and removed, and the mounting step is convenient.

A circular ring capable of rotating circumferentially is arranged at a bottom of the screw tail 1. A lower end face of the circular ring is relatively rotatably connected with a side face of the screw tail 1.

In order to improve the stability and flexibility of connection between the screw tail 1 and the ball screw 3, the chucking appliance 2 is also arranged on the screw tail 1. The screw tail 1, the chucking appliance 2 and the ball screw 3 are detachably connected with one another. The chucking appliance 2 limits the ball screw 3 and the screw tail 1 to prevent disconnection.

Figure 10:
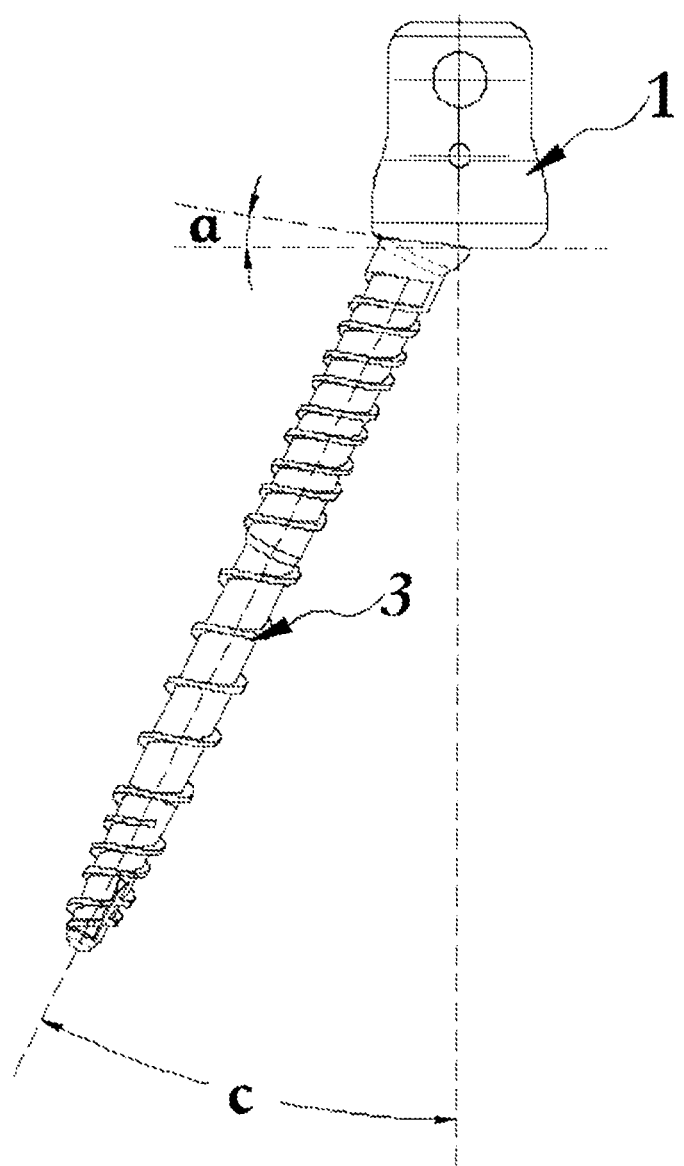
FIG. 10 is a deviation included angle c between the screw tail and the screw rod member in the screw of the present disclosure.
Figure 11:
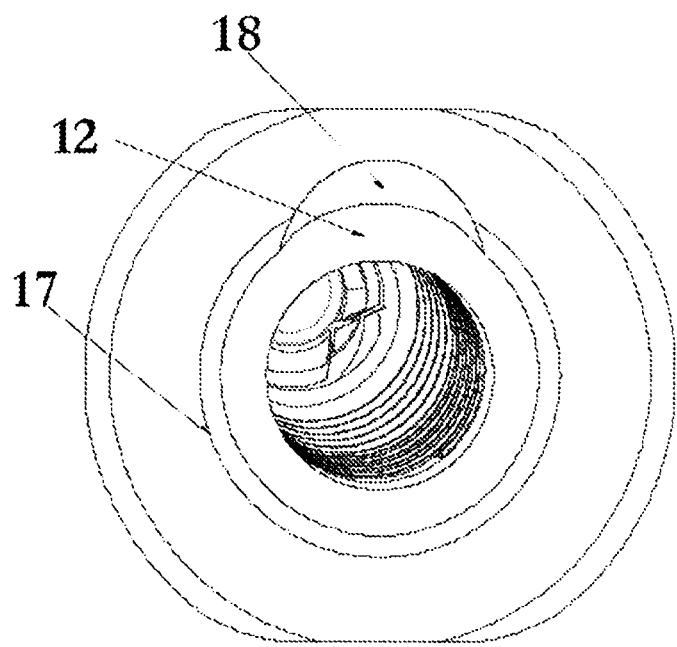
FIG. 11 is a bottom view of a bottom of the screw tail of FIG. 1.

In one embodiment, as shown in FIG. 10, an inclined bottom plate 17 capable of circumferentially rotating is arranged at a bottom of the screw tail 1. A lower end face of the inclined bottom plate 17 is oblique. One edge of a side wall of the inclined bottom plate 17 is long, and the other edge is short, so that the ball screw 3 rotates, swings and tilts towards a short side wall of the screw tail 1 by a larger angle c.

Figure 12:
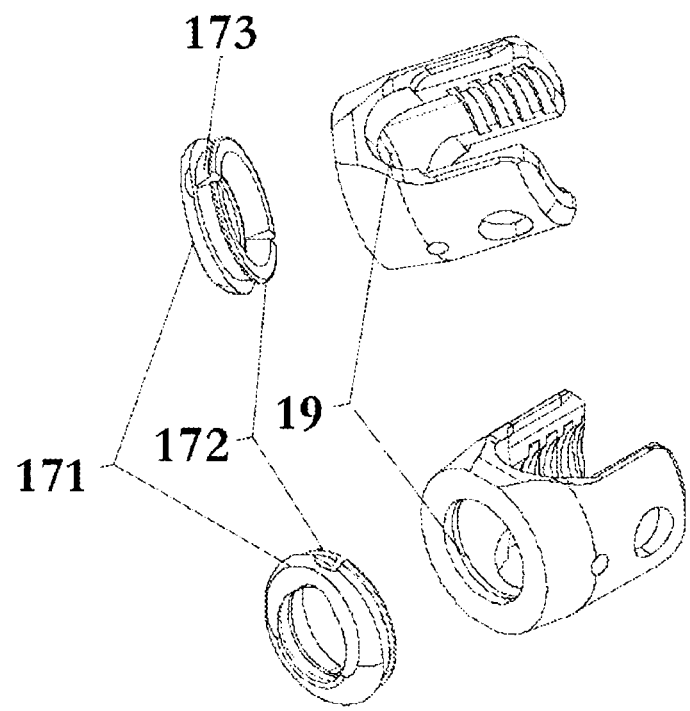
FIG. 12 is an exploded diagram of another embodiment of the screw tail.
Figure 13:
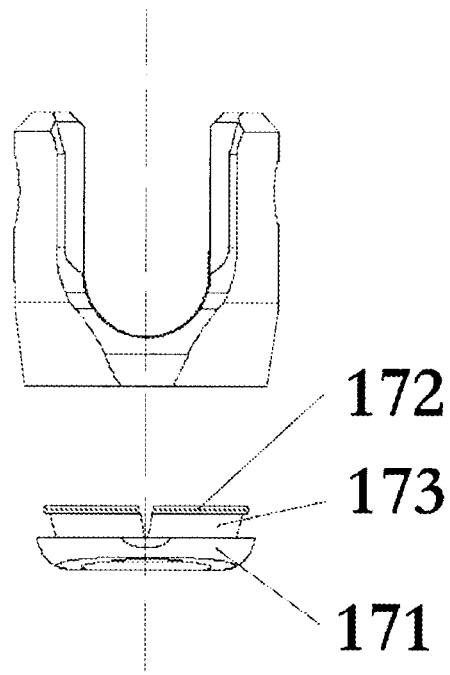
FIG. 13 is another front view of the screw tail in FIG. 12.

In one embodiment, as shown in FIG. 12 and FIG. 13, the inclined bottom plate 17 includes an inclined bottom plate lower component 171, an inclined bottom plate middle connector 173 connected with an upper end of the inclined bottom plate lower component 171, and an inclined bottom plate upper component 172 connected with an upper end of the inclined bottom plate middle connector 173; and the inclined bottom plate upper component 172 is rotatably clipped into a bayonet 19 formed in an inner side wall of the screw tail 1.

In one embodiment, as shown in FIG. 12 and FIG. 13, the inclined bottom plate upper component 172 is an annular convex ring; and the bayonet 19 is an annular inner notch clamped with the annular convex ring in a matched manner.

A through hole 12 penetrating through along an axial direction is formed in the screw tail 1. An opening in one end of the through hole 12 is large, and an opening in the other end is small. The ball screw 3 passes through the end of the through hole 12 with the large opening, and the ball head portion 32 is movably clamped at the other end of the through hole 12 with the small opening. The chucking appliance 2 is restrained in the through hole 12, so as to limit the degree of freedom of movement of the ball head portion 32 along an axial direction of the screw tail 1. An inner slot 23 is formed in one end of the chucking appliance 2. A top end of the ball head portion 32 is a plane 33, and a bottom end of the chucking appliance 2 is also a plane. The inner slot 23 is of an indented structure with a curved spherical surface, which is similar to the ball head portion 32 so that the inner slot 23 is buckled with the ball head portion 32 of the ball screw 3 in a matched manner. The ball screw 3 can freely rotate in the indented structure with a curved spherical surface, which further ensures the stability of the ball head portion 32 in the rotating process.

The through hole 12 along an inserting direction of the ball screw 3 includes a straight hole section 14 and a fixed section 15 which are connected with each other in a penetrating manner, and the chucking appliance 2 is located between the straight hole section 14 and the fixed section 15. An outer diameter of the chucking appliance 2 is greater than an inner diameter of the straight hole section 14. Symmetric U-shaped notches 11 are formed in a side wall of the screw tail 1. The U-shaped notches 11 are used for clipping and positioning the connection rod 4. The connection rod 4 is clipped between the U-shaped notches 11 of the screw tail 1 of each screw. A U-shaped gap 25 matched with the bottoms of the U-shaped notches 11 is arranged above the chucking appliance 2 to ensure stable clipping of the connection rod 4. An internal thread 13 is arranged on an inner wall of the straight hole section 14 of one side of the straight hole section 14 away from the chucking appliance 2. The internal thread 13 can be used for positioning and connecting an external bolt or an external positioning screw, so that each screw is connected into a whole framework for surgical positioning.

The fixed section 15 includes an upper first curved section and a lower second curved section which are communicated with each other, and a curvature of the second curved section is less than that of the first curved section. A side wall bevel of the first curved surface in the screw tail 1 has an included angle of about 5° relative to a plumb line. The first curved section is located on one side close to the chucking appliance 2, and a side wall clamping section 24 of the chucking appliance 2 is clamped with the first curved section in a matched manner. The chucking appliance 2 adopts an elastic member. A round hole groove 16 is formed in the side wall of the screw tail 1 that is provided with the straight hole section 14. An external die thimble component is inserted into the round hole groove 16 to press the chucking appliance 2, so that the chucking appliance 2 deforms to be separated from the screw tail 1 and then is restored to the original shape.

Figure 8:
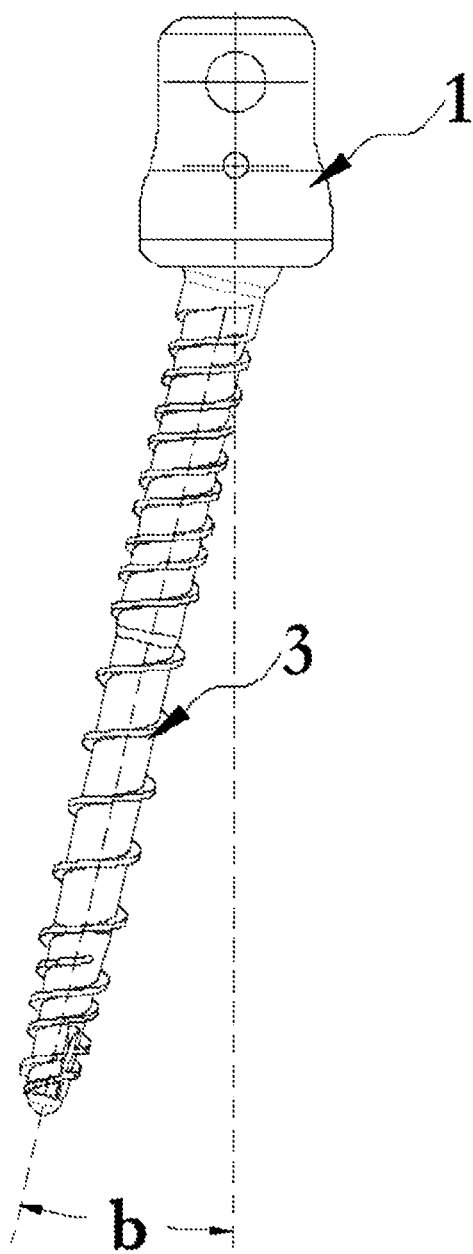
FIG. 8 is a deviation included angle b between a screw tail and a screw rod member in a screw in the prior art.
Figure 9:
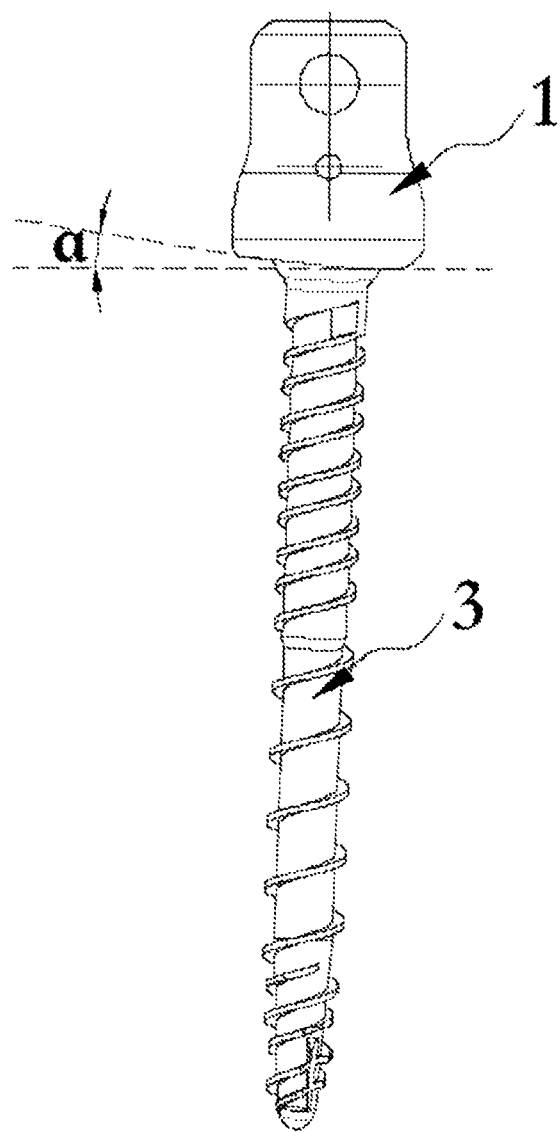
FIG. 9 is an included angle a between a lower end face of the screw tail in the screw of the present disclosure and a horizontal plane.

In the actual use of the cortical bone screw in surgical positioning, a screw implanting angle and the installation of the connection rod 4 will be affected due to the special blockage of the structure of the vertebral pedicle isthmus 7. As shown in FIG. 8, the included angle b between the ball screw 3 and the screw tail 1 of the existing screw can be adjusted to a small extent. An incision needs to be exposed to the vertebral pedicle isthmus 7 of the lower vertebral body 9 during the implantation, which increases the length of the incision. If the needle inserting point and the needle inserting angle of the lower vertebral body 9 can be changed, and the exposure range is reduced while keeping the supporting strength unchanged, the operation will be more minimally invasive. Therefore, the research and development personnel will make the lower end face of the screw tail 1 close to the ball head portion 32 into an oblique structure, to form the inclined bottom plate 17. Under the condition of reducing the amount of product materials and not damaging the main structure, the ball screw 3 rotates and tilts a larger angle towards the short side wall of the screw tail 1 relative to the screw tail 1. Under the condition that the included angle a between the lower end face of the screw tail 1 and the horizontal plane is 10°-30°, the implanting angle of the ball screw 3 still can be further increased, which reduces the length of the incision, and the operation is more minimally invasive. In some embodiments, the lower end face of the screw tail 1 forms an included angle of 20° relative to the horizontal plane. In order to improve the optimal design, without changing the main structure of the screw, a gap 18 is formed in the lower end in the short side wall direction, so that when the ball screw 3 rotates towards the short side wall of the screw tail 1, the ball screw 3 is clamped to the gap 18, thus increasing the inclination angle of the ball screw 3 relative to the screw tail 1, which further improves the flexibility of screw implantation and further reducing the impact of the incision size. Due to the design of the inclined bottom plate 17 on the lower end face of the screw tail 1, when multiple tail cap cortical bone screws are needed, the direction of the screw tail 1 can be changed more conveniently. Angle c of FIG. 10 is greater than angle b of FIG. 8, so that the extension space of the cortical bone screw is broadened; and the multiple tail cap cortical bone screws can be easily connected in series, so that the adaptability is greatly improved.

Figure 14:
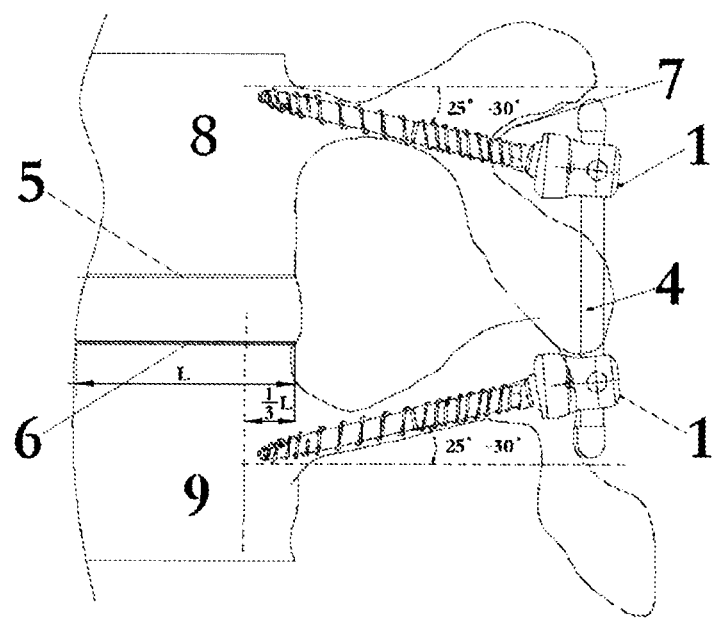
FIG. 14 is a front view showing positioning of the screw and a connection rod in a bone positioning device provided by the present disclosure.

The ball head portion 32 of the ball screw 3 is provided with a ball head positioning slot 34. The ball head positioning slot 34 and the chucking appliance 2 are coaxially arranged along a central hole 22 that is axially formed. To install the connection rod 4, the connection rod 4 is first clipped into the U-shaped notches 11, and then an external positioning pin or positioning bolt passes through an open pore on the connection rod 4 from the through hole 12 and then enters the ball head positioning slot 34. Thus, the connection rod 4 and the screw tail 1 of the screw are bolted together to form the schematic diagram as shown in the embodiment of FIG. 14.

In the actual operation, there are operation problems. Due to an error in a screw implantation orientation, it is necessary to change the direction of the U-shaped notches 11 on the basis of ensuring that the inclination angle of the ball screw 3 relative to the screw tail 1 remains the maximum constant, and re-implantation of the screw will make patients feel painful. In order not to change the shape of the cortical bone screw and to comply with the normal operation, the internal structure of the cortical bone screw is further researched and designed. The inclined bottom plate 17 at the bottom of the screw tail 1 is designed to rotate relative to the U-shaped notches 11. Even if the screw has been implanted, the U-shaped notches 11 need to be adjusted to place the connection rod 4. The U-shaped notches 11 can be adjusted when a side portion of the screw tail 1 above the inclined bottom plate 17 is rotated, ensuring that the original inclination angle of the ball screw 3 clipped to the gap 18 remains unchanged, which means that the gap 18 can be rotatably adjusted relative to the U-shaped notches 11. As shown in FIG. 12 and FIG. 13, the inclined bottom plate 17 of this design includes an inclined bottom plate lower component 171, an inclined bottom plate middle connector 173 connected with an upper end of the inclined bottom plate lower component 171, and an inclined bottom plate upper component 172 connected with an upper end of the inclined bottom plate middle connector 173; and the inclined bottom plate upper component 172 is rotatably clipped into a bayonet 19 formed in an inner side wall of the screw tail 1. In some embodiments, the inclined bottom plate upper component 172 is designed into an annular convex ring, and the bayonet 19 is an annular inner notch clamped with the annular convex ring in a matched manner. Any one of the inclined bottom plate middle connector 173 and the inclined bottom plate upper component 172 can adopt a semi-rigid deformable material in the prior art, which can retract when the inclined bottom plate upper component 172 is clipped into the bayonet 19, and is then restored after the inclined bottom plate upper component 172 is clipped into the bayonet 19. A deforming gap that facilitates deformation can also be formed in the annular convex ring. In the process of clipping the inclined bottom plate upper component 172 into the bayonet 19, the deforming gap is narrowed. After clipping, the deforming gap is restored. After the improvement, the entire shape of the screw is not destroyed. Therefore, the secondary fine adjustment flexibility of the cortical bone screw in the posterior surgical passage is improved without increasing the original impact of the vertebral pedicle isthmus 7. The patients feel less painful, and the surgical accuracy is improved.

Figure 15:
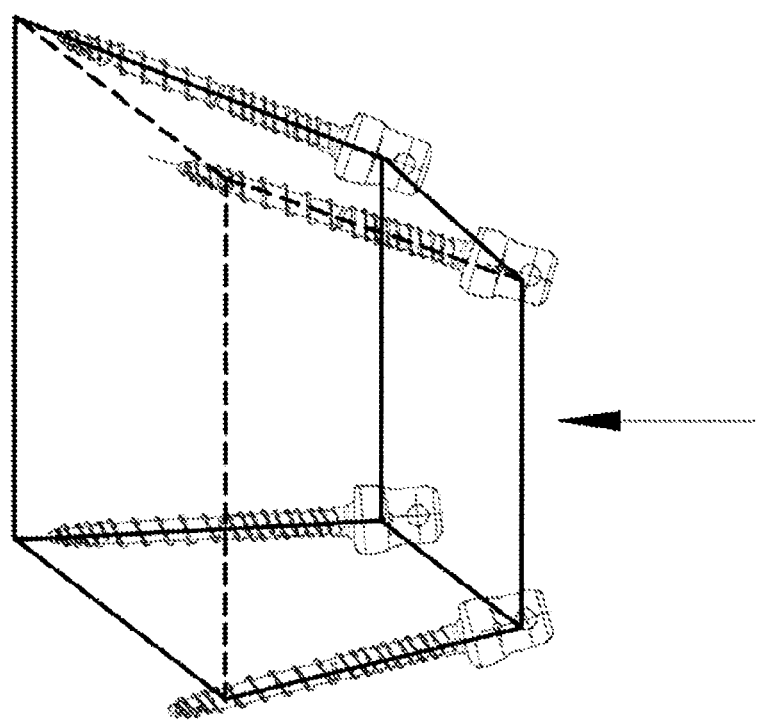
FIG. 15 is a schematic diagram of spatial arrangement of the screw in FIG. 14.

In most internal fixation operations for cortical bone trajectory screws, the screw inserting direction of the lower vertebral body 9 is kept being consistent with that of the upper vertebral body 8, that is, the screw inserting point is located at 5 o'clock (on the left side of a posteroanterior view) or 7 o'clock (on the right side of the posteroanterior view) below the vertebral pedicle isthmus 7, and a screw placement trajectory retracts 5-15°, most preferably 10°. Under a tail inclination of 25° to 30°, the screw is placed along the lower boundary of the vertebral pedicle. The screw is inserted from the needle inserting point from 5 o'clock to 11 o'clock (on the left side of the posteroanterior view), and the screw is inserted from the right side according to a mirror image. As shown in FIG. 15, in a direction shown by the back-front arrow, the tail of a screw canal for installing the screw of the present disclosure is converged. A bottom of an upper screw canal for installing the screw points to the posterior 1/3 position of an upper end plate 5, and a bottom of a lower screw canal points to the posterior 1/3 position of a lower end plate 6, so that the screw in the vertebral plate and the vertebral body is the longest and ends at a central position of the end plate of the vertebral body. In this way, an incision needs to be exposed to the vertebral pedicle isthmus 7 of the lower vertebral body 9, which increases the length of the incision. If a needle inserting point and a needle inserting angle of the lower vertebral body 9 are changed, and an exposure range is reduced under the condition of keeping the supporting strength unchanged, the operation can be more minimally invasive, bleeding in the operation is reduced, the operation time is shortened, and postoperative rehabilitation is accelerated.

Figure 16:
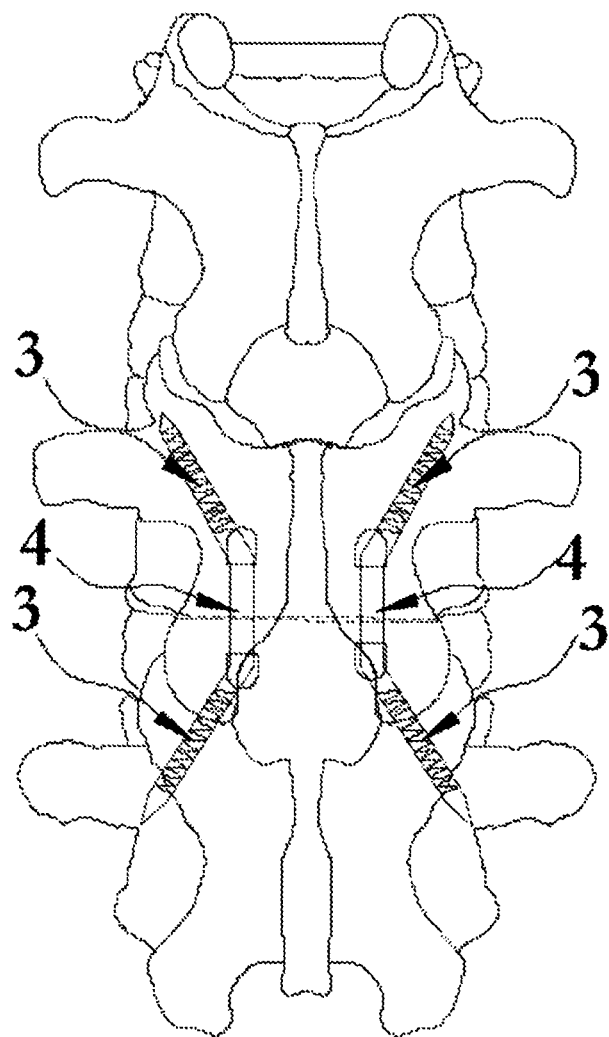
FIG. 16 is a side view in FIG. 14.

A use and positioning method of a multi-plane cortical bone screw provided by the present disclosure involves the above multi-plane cortical bone screw, and includes various positioning ways. The cortical bone is positioned by a bone positioning device as an embodiment. As shown in FIG. 14, FIG. 15 and FIG. 16, the bone positioning device includes a plurality of connection rods 4, and further includes a plurality of the above multi-plane cortical bone screws. The screw tails 1 are arranged in a spatial three-dimensional radial manner along side edges of a multi-edge platform, and the connection rods 4 used for positioning a bone are connected between the screw tails 1.

An assembling method includes: the screw inserting direction of the upper vertebral body 8 is the same as that in the existing method, that is, the screw inserting point is located at 5 o'clock (on the left side of the posteroanterior view) or 7 o'clock (on the right side of the posteroanterior view) below the vertebral pedicle isthmus 7; the screw placement trajectory retracts 5-15°, most preferably 10°; and under a tail inclination of 25° to 30°, the screw is placed along the lower boundary of the vertebral pedicle. The screw inserting point of the upper vertebral body 9 is changed, that is, the screw inserting point is located at 1 o'clock (on the left side of a posteroanterior view) or 11 o'clock (on the right side of the posteroanterior view) above the inferior articular process; the screw placement trajectory retracts 5-15° (most preferably 10°); and under a tail inclination of 25° to 30°, the screw is placed along the lower boundary of the vertebral pedicle. The screw is inserted from the needle inserting point from 1 o'clock to 7 o'clock (on the left side of the posteroanterior view), and the screw is inserted from the right side of the posteroanterior view according to a mirror image. A bottom of an upper screw canal used for mounting the screw points to the posterior 1/3 position of an upper end plate 5, and a bottom of a lower screw canal points to the posterior 1/3 position of a lower end plate 6, so that the screw in the vertebral plate and the vertebral body is the longest and ends at a central position of the end plate of the vertebral body.

The multi-plane cortical bone screw of the present disclosure can be pre-implanted into a cortical bone trajectory channel without blocking a surgical decompression area. The ball screw 3 cooperates with the screw tail 1 to rotatably adjust the position and angle of the screw tail 1, thus realizing a multi-plane adjustment function. The multi-plane cortical bone screw features with simple structure, convenience of operation, high applicability and the like.

It can be understood that the present disclosure is described by some embodiments. Those skilled in the art know that various changes or equivalent substitutions can be made to these features and embodiments without departing from the spirit and scope of the present disclosure. In addition, in the teachings of the present disclosure, these features and embodiments may be modified to adapt a particular situation and material without departing from the spirit and scope of the present disclosure. Therefore, the present disclosure is not limited by the specific embodiments disclosed herein, and all embodiments falling within the scope of the claims of the present application fall within the protection scope of the present disclosure.

The invention claimed is:

1. A multi-plane cortical bone screw, comprising a screw tail (1), a ball screw (3) connected with the screw tail (1), and a limiting buckle (2) arranged on the screw tail (1),
wherein a ball head portion (32) is arranged at an end of the ball screw (3), and a thread portion (31) is arranged at another end of the ball screw (3); the ball head portion (32) and the screw tail (1) are in universal connection, and the limiting buckle (2) limits the ball screw (3) and the screw tail (1) to prevent disconnection, so that the ball screw (3) is able to rotate along a conical surface relative to the screw tail (1), and a function of multi-plane multi-angle adjustment for the ball screw (3) relative to an axial line of the screw tail (1) is realized;
wherein a lower end face of the screw tail (1) close to the ball head portion (32) is relatively rotatably connected with a side face of the screw tail (1);
an inclined bottom plate (17) capable of circumferentially rotating is arranged at a bottom of the screw tail (1); a lower end face of the inclined bottom plate (17) is oblique; and a side wall of the inclined bottom plate (17) is long, and another side wall of the inclined bottom plate is short, so that the ball screw (3) rotates, swings and tilts towards a short side wall of the screw tail (1) by a larger angle c,
wherein an inner slot (23) is formed in an end of the limiting buckle (2); and the inner slot (23) is of an indented structure with a curved spherical surface, which is similar to the ball head portion (32) so that the inner slot (23) is buckled with the ball head portion (32) of the ball screw (3) in a matched manner.

2. The multi-plane cortical bone screw according to claim 1, wherein the inclined bottom plate (17) comprises an inclined bottom plate lower component (171), an inclined bottom plate middle connector (173) connected with an upper end of the inclined bottom plate lower component (171), and an inclined bottom plate upper component (172) connected with an upper end of the inclined bottom plate middle connector (173); and the inclined bottom plate upper component (172) is rotatably clipped into a bayonet (19) formed in an inner side wall of the screw tail (1).

3. The multi-plane cortical bone screw according to claim 2, wherein the inclined bottom plate upper component (172) is an annular convex ring; and the bayonet (19) is an annular inner notch clamped with the annular convex ring in a matched manner.

4. The multi-plane cortical bone screw according to claim 3, wherein the lower end face of the screw tail (1) and a horizontal plane form an included angle a of 10°-30°.

5. The multi-plane cortical bone screw according to claim 2, wherein the lower end face of the screw tail (1) and a horizontal plane form an included angle a of 10°-30°.

6. The multi-plane cortical bone screw according to claim 1, wherein a through hole (12) of the ball screw (3) comprises a fixed section; the fixed section comprises an upper first curved section and a lower second curved section which are communicated with each other, and a curvature of the second curved section is less than that of the first curved section; the first curved section is located on a side of the fixed section close to the limiting buckle (2); and a side wall clamping section (24) of the limiting buckle (2) is clamped with the first curved section in a matched manner.

7. The multi-plane cortical bone screw according to claim 6, wherein the lower end face of the screw tail (1) and a horizontal plane form an included angle a of 10°-30°.

8. The multi-plane cortical bone screw according to claim 1, wherein a through hole (12) of the ball screw (3) comprises a straight hole section (14); a round hole groove (16) is formed in a side wall of the screw tail (1) that is provided with the straight hole section (14); an external die thimble component is inserted into the round hole groove (16) to press the limiting buckle (2), so that the limiting buckle (2) deforms to be separated from the screw tail (1) and then is restored to an original shape.

9. The multi-plane cortical bone screw according to claim 8, wherein the lower end face of the screw tail (1) and a horizontal plane form an included angle a of 10°-30°.

10. The multi-plane cortical bone screw according to claim 1, wherein a gap (18) is formed in a top of the lower end face of the screw tail (1) close to the ball head portion (32), so that when the ball screw (3) rotates towards the gap (18), the ball screw (3) is clamped to the gap (18), thus increasing an inclination angle of the ball screw (3) relative to the screw tail (1).

11. The multi-plane cortical bone screw according to claim 10, wherein the lower end face of the screw tail (1) and a horizontal plane form an included angle a of 10°-30°.

12. The multi-plane cortical bone screw according to claim 1, wherein the lower end face of the screw tail (1) and a horizontal plane form an included angle a of 10°-30°.

13. The multi-plane cortical bone screw according to claim 1, wherein the lower end face of the screw tail (1) and a horizontal plane form an included angle a of 10°-30°.

14. A bone positioning device, comprising a plurality of connection rods (4) and further comprising a plurality of multi-plane cortical bone screws, wherein each multi-plane cortical bone screw comprises a screw tail (1), a ball screw (3) connected with the screw tail (1), and a limiting buckle (2) arranged on the screw tail (1), wherein a ball head portion (32) is arranged at an end of the ball screw (3), and a thread portion (31) is arranged at another end of the ball screw (3); the ball head portion (32) and the screw tail (1) are in universal connection, and the limiting buckle (2) limits the ball screw (3) and the screw tail (1) to prevent disconnection, so that the ball screw (3) is able to rotate along a conical surface relative to the screw tail (1), and a function of multi-plane multi-angle adjustment for the ball screw (3) relative to an axial line of the screw tail (1) is realized;

wherein a lower end face of the screw tail (1) close to the ball head portion (32) is relatively rotatably connected with a side face of the screw tail (1);

an inclined bottom plate (17) capable of circumferentially rotating is arranged at a bottom of the screw tail (1); a lower end face of the inclined bottom plate (17) is oblique; and a side wall of the inclined bottom plate (17) is long, and another side wall of the inclined bottom plate is short, so that the ball screw (3) rotates, swings and tilts towards a short side wall of the screw tail (1) by a larger angle c; and wherein the screw tails (1) are arranged in a spatial three-dimensional radial manner along side edges of a multi-edge platform, and the connection rods (4) used for positioning a bone are connected between the screw tails (1) of each group, wherein each group comprises two screw tails, wherein an inner slot (23) is formed in an end of the limiting buckle (2); and the inner slot (23) is of an indented structure with a curved spherical surface, which is similar to the ball head portion (32) so that the inner slot (23) is buckled with the ball head portion (32) of the ball screw (3) in a matched manner.

15. The bone positioning device according to claim 14, wherein the inclined bottom plate (17) comprises an inclined bottom plate lower component (171), an inclined bottom plate middle connector (173) connected with an upper end of the inclined bottom plate lower component (171), and an inclined bottom plate upper component (172) connected with an upper end of the inclined bottom plate middle connector (173); and the inclined bottom plate upper component (172) is rotatably clipped into a bayonet (19) formed in an inner side wall of the screw tail (1).

16. The bone positioning device according to claim 15, wherein the inclined bottom plate upper component (172) is an annular convex ring; and the bayonet (19) is an annular inner notch clamped with the annular convex ring in a matched manner.

17. The bone positioning device according to claim 14, wherein a through hole (12) of the ball screw (3) comprises a fixed section; the fixed section comprises an upper first curved section and a lower second curved section which are communicated with each other, and a curvature of the second curved section is less than that of the first curved section; the first curved section is located on a side of the fixed section close to the limiting buckle (2); and a side wall clamping section (24) of the limiting buckle (2) is clamped with the first curved section in a matched manner.

18. The bone positioning device according to claim 14, wherein a through hole (12) of the ball screw (3) comprises a straight hole section (14); a round hole groove (16) is formed in a side wall of the screw tail (1) that is provided with the straight hole section (14); an external die thimble component is inserted into the round hole groove (16) to press the limiting buckle (2), so that the limiting buckle (2) deforms to be separated from the screw tail (1) and then is restored to an original shape.

\* \* \* \* \*